(12) United States Patent
Walter et al.

(10) Patent No.: US 11,931,462 B2
(45) Date of Patent: Mar. 19, 2024

(54) METHOD FOR PRODUCT TRACKING IN AN INSTALLATION

(71) Applicant: Fette Compacting GmbH, Schwarzenbek (DE)

(72) Inventors: Nicolas Walter, Hamburg (DE); Alexander Evers, Bargteheide (DE)

(73) Assignee: Fette Compacting GmbH, Schwarzenbek (DE)

( * ) Notice: Subject to any disclaimer, the term of this patent is extended or adjusted under 35 U.S.C. 154(b) by 199 days.

(21) Appl. No.: 17/349,138

(22) Filed: Jun. 16, 2021

(65) Prior Publication Data

US 2021/0386675 A1 Dec. 16, 2021

(30) Foreign Application Priority Data

Jun. 16, 2020 (DE) .................. 10 2020 115 777.0

(51) Int. Cl.
*A61K 9/20* (2006.01)
*A61J 3/07* (2006.01)
*A61J 3/10* (2006.01)
*B30B 15/30* (2006.01)
*G01G 13/24* (2006.01)
*G01G 17/00* (2006.01)
(Continued)

(52) U.S. Cl.
CPC ............. *A61K 9/2095* (2013.01); *A61J 3/074* (2013.01); *A61J 3/10* (2013.01); *B30B 15/302* (2013.01); *G01G 13/24* (2013.01); *G01G 17/00* (2013.01); *G01G 19/414* (2013.01); *G06Q 10/08* (2013.01)

(58) Field of Classification Search
CPC ........... A61K 9/2095; A61J 3/074; A61J 3/10; B30B 15/302; G01G 13/24; G01G 17/00; G01G 19/414; G06Q 10/08
See application file for complete search history.

(56) References Cited

U.S. PATENT DOCUMENTS 3,646,631 A * 3/1972 Wurst ............... A61J 3/074
15/88.2
4,811,802 A * 3/1989 Yamamoto .......... G01G 13/24
177/1
(Continued)

FOREIGN PATENT DOCUMENTS

DE  4018428 A1  12/1991
DE  4309978 C1  6/1994
(Continued)

OTHER PUBLICATIONS

IN Application No. 202114026086; filed Nov. 6, 2021; Indian Office Action dated Nov. 1, 2022 (13 pages).

*Primary Examiner* — Randy W Gibson
(74) *Attorney, Agent, or Firm* — Barclay Damon LLP

(57) ABSTRACT

A method for tracking product in an installation in which powdered product is processed into manufactured items is provided. The method comprises introducing the powdered product into the installation through at least one inlet, obtaining measurement data for the powdered product from at least one mass sensor positioned in the at least one inlet, and dividing the measurement data into mass units of equal size. The progression of the mass units is then tracked through the installation using measurement data from at least one other mass sensor in the installation.

20 Claims, 3 Drawing Sheets

(51) Int. Cl.
  *G01G 19/414*  (2006.01)
  *G06Q 10/08*   (2023.01)

(56) References Cited

U.S. PATENT DOCUMENTS

| | | | | |
|---|---|---|---|---|
| 5,103,401 | A | * | 4/1992 | Johnson ................. G01G 13/29 |
| | | | | 177/105 |
| 5,114,630 | A | | 5/1992 | Newman et al. |
| 7,279,644 | B1 | * | 10/2007 | Kasel ..................... G01G 11/00 |
| | | | | 177/125 |
| 2012/0061869 | A1 | | 3/2012 | Boeckx et al. |
| 2016/0311565 | A1 | * | 10/2016 | Scheffler ................. A61J 3/074 |
| 2018/0271791 | A1 | * | 9/2018 | Myerson ............... A61K 9/2095 |
| 2020/0016552 | A1 | | 1/2020 | Gebauer et al. |
| 2021/0394133 | A1 | * | 12/2021 | Walter .................. B01F 35/832 |
| 2022/0054359 | A1 | * | 2/2022 | Singh .................... B65B 57/145 |

FOREIGN PATENT DOCUMENTS

| | | |
|---|---|---|
| DE | 202015107010 U1 | 3/2016 |
| DE | 102015103245 B3 | 6/2016 |
| DE | 102016218135 A1 | 3/2018 |
| EP | 2427166 | 11/2010 |
| WO | 2008/149190 A1 | 12/2008 |
| WO | 2010/128359 A1 | 11/2010 |

* cited by examiner

METHOD FOR PRODUCT TRACKING IN AN INSTALLATION

CROSS REFERENCE TO RELATED INVENTION

This application is based upon and claims priority to, under relevant sections of 35 U.S.C. § 119, German Patent Application No. 10 2020 115 777.0, filed Jun. 16, 2020, the entire contents of which are hereby incorporated by reference.

FIELD OF TECHNOLOGY

The disclosure relates to a method for product tracking in an installation in which powdered product is processed into manufactured items.

BACKGROUND

In such installations, powdered products for example are processed into tablets or capsules. Correspondingly, the installations can for example include a tablet press or a capsule filling machine. Such installations have one or more product inlets for the powdered product to be processed in the installation. To the extent that several product inlets are provided for different products, such installations normally also have a mixing apparatus in which the products are mixed to form the product to be pressed. The mixed product is then fed from the mixing apparatus to for example a tablet press, for example a rotary tablet press, where the product mixture is pressed into tablets. The produced tablets pass out of the installation through a tablet outlet in the tablet press. Such installations can be designed as continuous installations in which the product fed continuously to the installation is processed continuously in contrast to a batch process, for example into tablets or capsules. Moreover, so-called containment installations are known that, by special sealing measures, largely prevent product dust from exiting into the environment.

In particular with continuously working installations, there is a need for the product fed to the installation at the inlet to be assigned to manufactured items produced in the installation. This is necessary when the product for example is recognized as being faulty by sensors in the installation. In this case, the manufactured items produced from this product, for example tablets or capsules, must be removed, wherein to avoid unnecessary scrap, only the manufactured items produced from the corresponding product batch should be removed if possible. There is correspondingly a need for product tracking in the installation.

So-called dwell time models for product tracking are known in which the produced manufactured items are assigned to the product fed into the system using the dwell time, or respectively throughput time, of the product through the installation. Product tracking based on such dwell time models is however complicated, in particular when several different products are fed into the system. Accordingly, the dwell time can differ depending on the fed products. The dwell time must correspondingly be reestablished for each product combination in order to achieve reliable results. Moreover, the precision of dwell time models strongly depends on the operating point of the installation, i.e., the operating parameters set in each case. This is of course readily apparent with regard to the production speed of the installation. However, the dwell time also depends on other operating parameters such as the mode of operation of a mixing apparatus. Even small deviations from an operating point must be taken into account in the dwell time model. How such a deviation from an operating point affects the dwell time must be reestablished experimentally each time, in particular also depending on the particular product. The effort in parameterizing a dwell time model to achieve an acceptable accuracy is therefore very high.

Starting from the explained prior art, the object of the invention is to provide a method of the aforementioned type by means of which product tracking in an installation in a simple and precise way is possible in which powdered product is processed into manufactured items.

BRIEF SUMMARY OF THE INVENTION

The invention achieves the object for a method of the aforementioned type in that the product introduced into the installation is divided into mass units by using measurement data from at least one inlet mass sensor arranged at a product inlet of the installation, and the progress of the mass units in the installation is tracked by using measurement data from at least one other mass sensor in the installation.

Embodiments of the installation can include one or more product inlets for the product to be processed in the installation. The installation can moreover include a mixing apparatus for mixing different products fed to the installation. The installation also includes a production machine such as a tablet press, for example a rotary tablet press, or a capsule filling machine in which the product fed to the installation, or respectively the product mixture produced in the mixing apparatus is processed for example into manufactured items such as tablets or capsules. The produced manufactured items can for example be oral, solid forms of administration (oral solid dosages, OSD). The installation has an inlet mass sensor arranged at a product inlet that determines the weight, or respectively the mass of the product fed to the installation. On the basis of this determination of mass, the product fed to the installation is for example divided into sequential mass units in an evaluation and control apparatus of the installation. The installation has at least one additional mass sensor that is downstream from at least one inlet mass sensor in the direction of flow of the product and determines the mass, or respectively the weight of the product flowing through the installation. The progress of the mass units in the installation is tracked on this basis. This product tracking is accomplished in particular by means of an evaluation apparatus of the installation, preferably on the basis of evaluation algorithms. The mass sensors can directly measure the mass, i.e., can include a weighing apparatus, or can directly measure the mass flow. They can however also indirectly measure the mass or the mass flow.

In contrast to the prior art, the invention does not propose time-based, but rather mass-based product tracking. The mass units, or respectively mass quanta are small enough to ensure sufficient precision in product tracking for the particular intended application. For example, the mass units can have a size of less than 50 g. In particular, fluctuations in the flow speed, or respectively production speed in/of the installation can possess a lower frequency than the frequency of the sequential mass units. This renders the product tracking largely independent from fluctuations in the flow, or respectively production speed, and therefore from corresponding deviations from a certain operating point of the installation. Product tracking, for example the recording of mass units at the outlet of a tablet press or a capsule filling machine, or respectively the installation, and assignment based there-upon to a product, or respectively a product batch fed to the installation is consequently reliable, and is possible while minimizing the scrap when a faulty product batch is recognized.

In the evaluation unit, the mass units are moved through the installation similar to a shift register model. It has been shown that the reference to mass in product tracking according to the invention has implicit properties which can only be achieved in a time-based model (dwell time model) by using higher order equations in corresponding evaluation algorithms. The number of necessary parameters for adapting to a certain product, or respectively an operating point of the installation is thereby reduced significantly in comparison to a conventional dwell time model. At the same time, it is possible according to the invention to also observe material properties that do not relate to the concentration or dwell time in a part of the installation. This results from the basic structure of product tracking according to the invention similar to a shift register for finite mass units. In an extreme case, it is therefore possible to mark a single mass unit as defective or for sampling, and to remove it from the installation at a later time.

According to an embodiment, the progress of the mass units in the installation can be tracked in real time. This enables an alignment of the product tracking model, in particular the corresponding algorithms, with other sensor data from the installation. The robustness and the long-term stability of the product tracking model can thereby be further increased.

As already mentioned, the installation can be an installation for tablet production in which powdered product is pressed into tablets in a tablet press. The installation can therefore include a tablet press, for example a rotary tablet press.

According to another embodiment, the progress of the mass units in the installation can be tracked by using measurement data from another mass sensor arranged at a tablet outlet of the tablet press. This additional mass sensor can for example be a sensor with which the number of tablets discharged by the tablet press is counted. Their weight can be assumed to be known for a given process. Weight, or respectively mass, can be determined indirectly by tablet counting. It would however of course also be possible for the other mass sensor to count and weigh the discharged tablets. In the aforementioned embodiment, the produced tablets are assigned directly to a corresponding mass unit at the inlet, and therefore to a corresponding product batch.

According to another embodiment, the progress of the mass units in the installation can be tracked by using measurement data from another mass sensor arranged at a filling apparatus of the tablet press. This mass sensor can in turn measure the mass or the mass flow directly or indirectly. The filling apparatus of a tablet press generally possesses a filling tube through which the powdered product is fed to a filling chamber from which it is added to cavities of a die plate of the press where it is then pressed by upper and lower punches of the tablet press. A filling reservoir can be upstream from the filling tube. The additional mass sensor can for example be arranged on the filling tube, the filling reservoir or the filling chamber.

The installation can also be an installation for capsule production in which powdered product is added to capsules in a capsule filling machine. The installation can then correspondingly include a capsule filling machine. The progress of the mass units in the installation can then for example be tracked by using measurement data from an additional mass sensor arranged at an outlet of the capsule filling machine. This additional mass sensor can for example be a sensor with which the number of capsules discharged from the capsule filling machine is counted. Their weight can be assumed to be known for a given process. Weight, or respectively mass, can be determined indirectly by capsule counting. It would however of course also be possible for the other mass sensor to count and weigh the discharged capsules.

According to another embodiment, it can be provided for the installation to include several product inlets for different powdered products and a mixing apparatus for mixing the different products into manufactured items before processing, for example before being pressed into tablets in a tablet press, or before filling capsules in a capsule filling machine, wherein the product added to the installation is divided into mass units by using measurement data from several inlet mass sensors arranged at the product inlets of the installation.

The progress of the mass units in the installation can then be tracked by using measurement data from at least one additional mass sensor arranged on the mixing apparatus. Different products fed to the installation can for example be an active pharmaceutical ingredient (API), an excipient, and/or a lubricant. The different products are fed to the installation through separate inlets from which they are fed to the mixing apparatus where they are mixed into the product mixture to be pressed. The mixing apparatus can for example include a mixing screw. The product is therefore simultaneously conveyed while being mixed.

According to another embodiment, a mixing of different mass units into new mass units in the mixing apparatus can be taken into account when tracking the progress of the mass units in the installation. In taking into account the mixing, a mixing ratio achieved by the mixing apparatus can be taking into account. Accordingly, new mass units that contain the mixed product are formed from the mass units arriving from the mixing apparatus. The mixture ratio of the mixing apparatus is dependent on the specification for the mixing apparatus and possibly the feed rate for the individual products. The mixture ratio is therefore known for the particular product and can be used when taking mixing into account. When the mixing apparatus for example mixes two products evenly at a 50% to 50% ratio, the new mass units contain one half of the first and the second product each. In other mixture ratios achieved by the mixing apparatus, there is correspondingly a different division into the new mass units. The mass units mix together in the mixing apparatus depending on the known mixture ratio. This can for example be taken into account by forming a moving average over sequential mass units, and new mass units are formed from the formed average. In this manner, the extent to which certain mass units have components from different product batches from the different product inlets can be calculated.

In addition to the mixing apparatus, a mixture, or respectively a dispersion can also occur in other components of the installation in which an agitator mixes product batches or, for example in a filling apparatus of a tablet press. To track the progress of the mass units in the installation, a mixing of different mass units into new mass units can accordingly also be taken into account in other components of the installation, for example in dosing apparatuses, or a tablet press, or a capsule filling machine. In taking into account the mixing, a mixing ratio achieved by the particular component can be taking into account. In turn, new mass units that contain the mixed product are formed from the arriving mass units of the particular component. The mixing ratio of the component is normally known for the particular process and can be used when taking into account mixing as explained with respect to the mixing apparatus.

According to another embodiment, a backmixing of different mass units can be taken into account when tracking the progress of the mass units in the installation. Such a backmixing in which the product changes between different mass units, for example from one mass unit into a preceding mass unit, can be desired or undesired. It is however generally specific to the particular installation. It therefore can be determined empirically beforehand and then taken into account in the algorithms for product tracking. Experiments using spectrometry can for example be performed to empirically determine the backmixing. The use of a so-called tracer material that can be clearly traced for example based on a certain coloring is also conceivable.

According to another embodiment, dead spaces for product in the installation can be taken into account when tracking the progress of the mass units. The product can collect in such dead spaces, or respectively dead zones, which then leaves the installation at a later time. Such dead spaces arise for example in screw conveyors for transporting the product within the installation. They can also be determined empirically since they are also generally specific to the particular installation and are then taken into account in the algorithms used for product tracking.

According to another embodiment, product loss in the installation, such as product loss from a suction apparatus in the installation, can be taken into account when tracking the progress of the mass units in the installation. In particular during long installation operating times, such product loss is significant and has to be compensated by replenishing more material. With time-based and dwell-time models, the parameters of the model would have to be changed with great effort to accomplish this. This is unnecessary according to the invention. The product loss can be determined by comparing the mass flow into the installation and out of the installation for a given product quantity, for example the number and the weight of manufactured items leaving the installation per unit time, for example tablet or capsule filling machines. Product loss can occur during routine suction in for example tablet presses to maintain an underpressure in the tablet press when a bit of product is suctioned in addition to air. Again, this product loss is generally specific to the particular installation and can be correspondingly determined empirically, for example in the above-explained manner.

The masses of the mass units can be the same according to a preferred embodiment. If all mass units possess the same mass, this simplifies tracing, in particular the algorithms used for product tracking. As explained above, the mass units have a sufficiently low mass for reliable and precise product tracking. According to an embodiment in this regard, the mass of the mass units can lie within a range of 1 g to 20 g, preferably within a range of 1 g to 10 g. In particular, all mass units can possess the same mass, wherein this same mass for all mass units is then a mass within the aforementioned ranges. The mass units are accordingly sufficiently small for precise product tracking and, if applicable, for a targeted removal of manufactured items of a faulty unit of measure while avoiding large amounts of scrap.

According to another embodiment, the plausibility of tracking the progress of the mass units in the installation can be evaluated by using measurement data from several mass sensors of the installation. In evaluating several measuring apparatuses to determine the mass of the mass units, a faulty determination of mass can be identified, for example when a drift is found when tracking the mass units.

The at least one product inlet of the installation can include at least one dosing apparatus, in particular a loss-in-weight dosing apparatus. Such dosing apparatuses are used for the dosed feeding of product. So-called loss-in-weight dosing apparatuses (LIW feeders) have a weighing apparatus and dose the product to be fed by measuring the weight of the product located in the dosing apparatus. This weighing apparatus can be used in a very practical manner as an inlet mass sensor.

As already explained, the invention is particularly suitable for installations for continuously processing the powdered product into manufactured items, for example for continuous tablet production or capsule filling. As is known per se, in installations for continuous manufacturing, the product is continuously fed into the installation in contrast to a batch process and is processed therein continuously into manufactured items, if applicable following a previous continuous mixing of the product. Such installations can theoretically run endlessly, wherein only sufficient product replenishment at the product inlets needs to be ensured. In comparison to batch installations, they have various advantages as is known per se to a person skilled in the art. Particularly with such installations for continuous manufacturing, precise and high-resolution product tracking as ensured according to the invention is of great importance.

Moreover, the installation can be a so-called containment installation that largely prevents product dust from exiting the installation due to special sealing measures. The containment level of an installation is determined for example according to the so-called SMEPAC test (standardized measurement of equipment particulate airborne concentration). The installation used in the method according to the invention can for example possess a containment level according to the SMEPAC test of 10-100 $\mu g/m^3$, or less than 10 $\mu g/m^3$.

BRIEF DESCRIPTION OF THE DRAWINGS

An exemplary embodiment of the invention is explained below in greater detail with reference to figures.

DETAILED DESCRIPTION OF THE INVENTION

Figure 1:
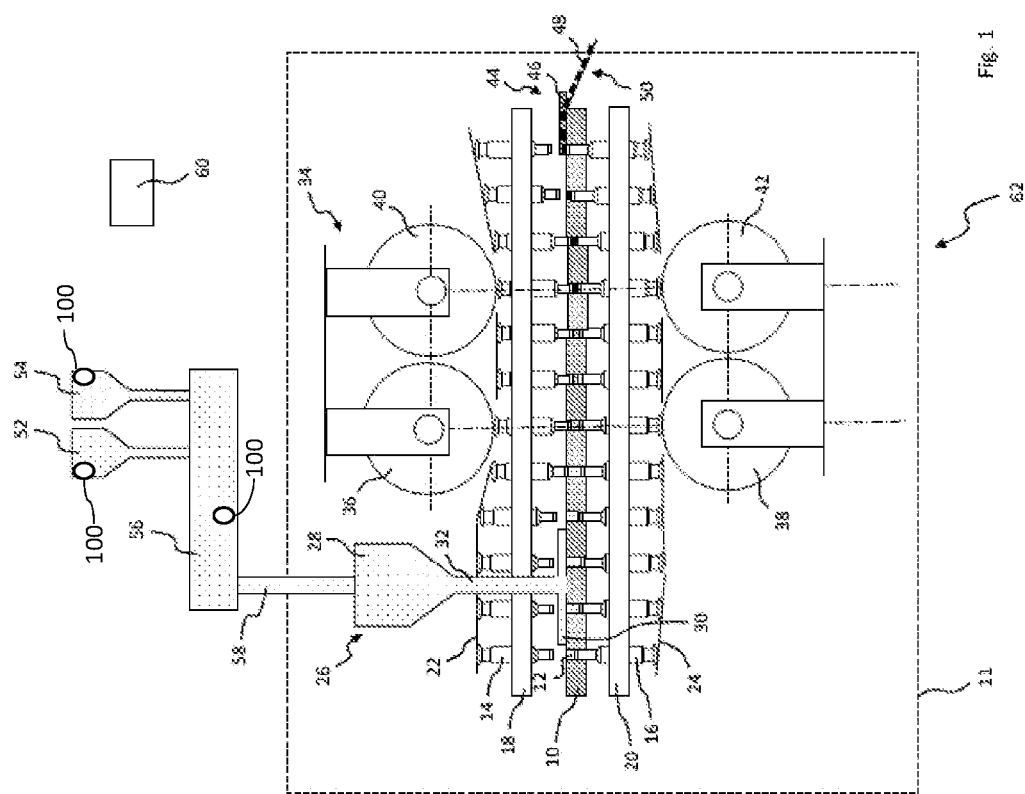
FIG. 1 illustrates a schematic depiction of an embodiment of a portion of an installation used for manufacturing tablets.

The same reference numbers refer to the same objects in the figures unless indicated otherwise. The embodiment of an installation shown in FIG. 1 is an installation for tablet production in which powdered product is pressed into tablets. As shown, the installation correspondingly includes a rotary press arranged in a housing 11, in particular a rotary tablet press with a rotor that is rotationally driven by a rotary drive with a die plate 10 which has a plurality of seats 12. The seats 12 may for example be formed by holes in the die plate 10. Furthermore, the rotor includes a plurality of upper punches 14 and lower punches 16 that rotate synchronously with the die plate 10. The upper punches 14 are axially guided in an upper punch guide 18 and the lower punches 16 are axially guided in a lower punch guide 20. The axial movement of the upper punches 14 and lower punches 16 during the rotation of the rotor is controlled by upper control cam elements 22 and lower control cam elements 24. The rotary press further comprises a filling apparatus 26 which comprises a filling reservoir 28 and a filling chamber 30, which are connected via a filling tube 32. In this way, the powdered filling material in the present example passes under the force of gravity from the filling tube 28 via the feed section 32 into the filling chamber 30, and passes therefrom via a filling opening provided in the bottom side of the filling chamber 30 into the receiving means 12 of the die plate 10, again under the force of gravity.

The rotary press further includes a pressing apparatus 34. The pressing apparatus 34 includes a pre-pressing apparatus with an upper pre-pressing roller 36 and a lower pre-pressing roller 38, as well as a main pressing apparatus with an upper main pressing roller 40 and a lower main pressing roller 42. Furthermore, the rotary press includes an ejection apparatus 44 and a scraping apparatus 46 having a scraping element which feeds the tablets 48 produced in the rotary press to a discharge apparatus 50 for discharging from the rotary press. The scraping apparatus 46 may for example comprise a preferably crescent-shaped scraping element, which scrapes tablets 48 conveyed by means of the lower punches 16 onto the top side of the die plate 10 off the die plate 10 in the region of the ejection apparatus 44 and feeds them to the discharge apparatus 50.

The housing 11 may be at a positive or negative pressure with respect to the surroundings of the housing 11. Moreover, the housing 11 may be sealed with respect to the surroundings. The rotary press may be a so-called containment press.

It is expressly noted that the rotary press shown in FIG. 1 with its explained features is only an example. In principle, any other tablet press is also suitable for the invention. In principle, any other type of production machine is also suitable for the invention in which powdered product is processed into manufactured items such as for example a capsule filling machine in which powdered product is added to capsules.

In the depicted example, the installation moreover includes two product inlets 52, 54 for two different products to be fed to the tablet press to be pressed into tablets 48, for example a pharmaceutical agent on the one hand and an excipient on the other hand. The product inlets 52, 54 can for example include dosing apparatuses, in particular loss-in-weight dosing apparatuses. The fed products pass from the product inlets 52, 54 to a mixing apparatus 56 of the installation in which the products are mixed to form the product mixture to be pressed. The mixing apparatus can for example include a mixing screw. The mixed product leaving the mixing apparatus 56 is fed via a feed line 58 to the filling reservoir 28 of the filling apparatus 26. The installation also includes an evaluation and control apparatus 60 for controlling the operation of the installation and for performing the product tracking according to the invention on the basis of evaluation algorithms saved in the evaluation and control apparatus 60. The product inlets 52, 54, the mixing apparatus 56, the filling apparatus 26 and the tablet press, in particular a tablet outlet of the tablet press, can each include at least one mass sensor 100 with which the mass, or respectively the weight of the product guided through the installation, or respectively tablets discharged from the installation, can be determined directly or indirectly. The evaluation and control apparatus 60 is connected to the mass sensors and if applicable to other sensors of the installation. In particular, it receives measurement data from the sensors and uses the data as a basis for control and evaluation. To accomplish this, the evaluation and control apparatus 60 can be connected to all components of the installation by corresponding connecting lines.

The method according to the invention for tracking product in the installation shown in FIG. 1 will be explained in greater detail with reference to FIG. 2 and FIG. 3. The product inlets 52, 54, the mixing apparatus 56 and the tablet press with reference number 62 are shown highly schematized. By using the measurement data from inlet mass sensors arranged at the product inlets 52, 54, the product added via the product inlets 52, 54 to the installation are each divided into mass units 64, 66 of equal size. The mass units 64, 66 of a first product batch are identified with the numbers 0 1, and mass units 64, 66 of a second product batch are identified with the numbers 1 0. At the beginning of the dispersion zone formed by the mixing apparatus 56, new mass units 68 are formed from the mass units 64, 66 from the two product inlets 52, 54 in which product components comprised of two mass units 64, 66 from both product inlets 52, 54 are contained in the mixing apparatus 56 corresponding to the known feed ratio. The feed ratio is for example considered to be the same for both product inlets 52, 54 in FIG. 2. For the mass units 64, 66 arranged at the very bottom below the mass unit chains located under the product inlets 52, 54 in FIG. 2, this means for example that two new mass units 68 are formed from these two mass units 64, 66 that are formed from one-half of each of the initial mass units 64, 66. The mass units 68 formed in this manner are identified corresponding to their composition with the numbers 0 1/1 0. One half of their mass is therefore comprised of product from the first product batch 0 1 from the first product inlet 52, and product from the second product batch 1 0 from the second product inlet 54.

Figure 2:
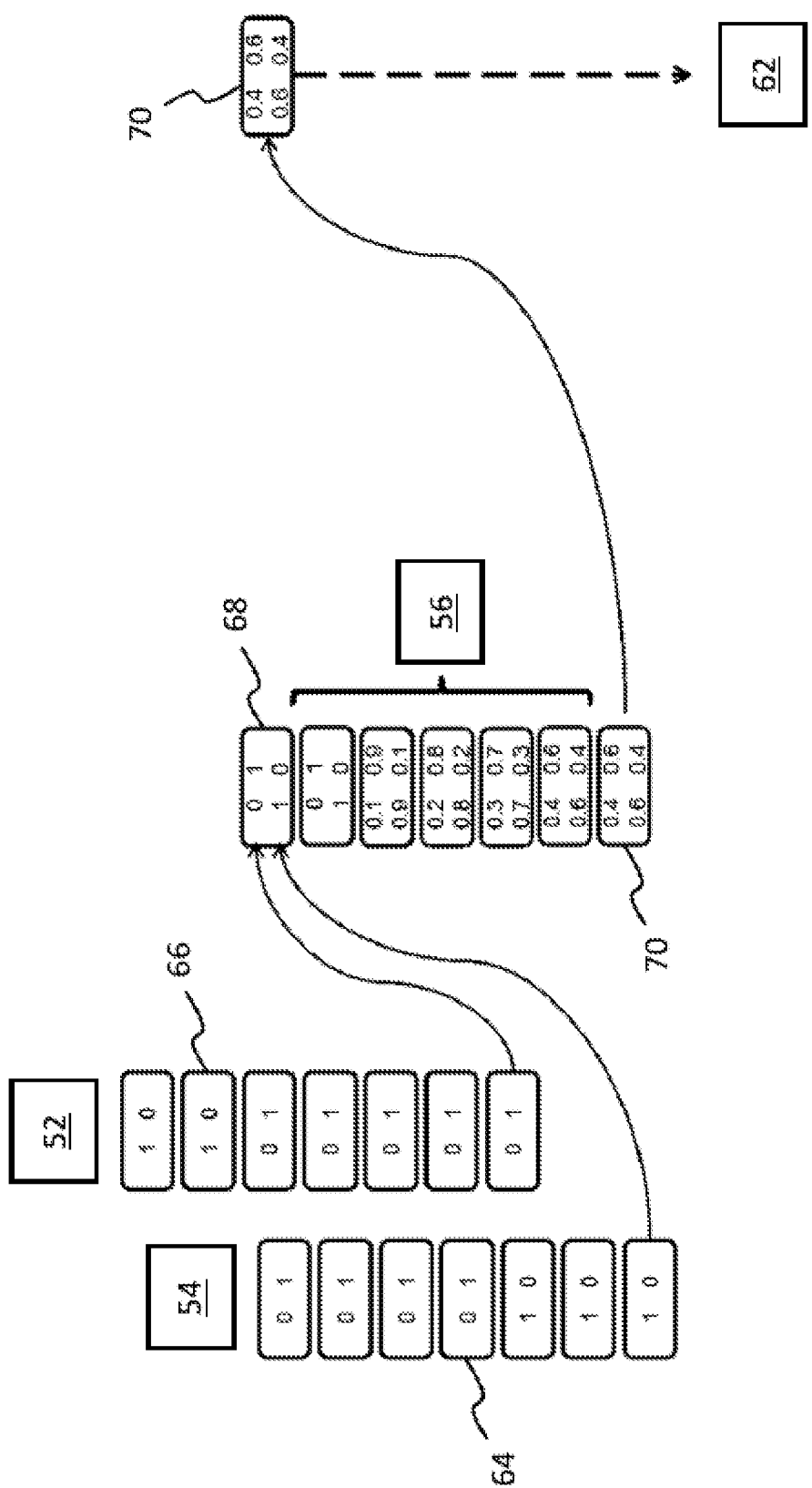
FIG. 2 illustrates a schematic diagram of an embodiment of a method for product tracking.

Corresponding to the also known, for example empirically determined mixing ratio of the mixing apparatus 56, the mixing of the components of the mass units in the dispersion zone formed by the mixing apparatus 56 is considered until achieving the mass units that can be seen at reference number 70 in FIG. 2. A mixture of sequential mass units 68 with each other also occurs in the dispersion zone. A mixture of product from the different initial product batches can also occur at the product inlets 52, 54. Mathematically, the mixture in the dispersion zone can for example be described as a shift register by forming a moving average comprising a sequential mass units 68. This causes the ratios of the components of the mass units 68 indicated by the number pairs to change. At the end of the dispersion zone, the formed mass units 70 are identified by the numbers $$\frac{0.4\ 0.6}{0.6\ 0.4}$$

in the shown example. This means that the mass units 70 in the shown example have 40% of the mass from the second product batch (1 0) of the first product inlet 52, and 60% of the mass from the first product batch (0 1) of the first product inlet 52. Moreover, this means that the mass units 70 have 60% of the mass from the second product batch (1 0) of the second product inlet 54, and 40% of the mass from the first product batch (0 1) of the second product inlet 52. Of course, these ratios change depending on the portion of the product from different product batches that is found in the mixing apparatus 56.

The mass units 70 are tracked in their progress through the installation, in particular to the tablet press 62, in particular by using measurement data from a mass sensor arranged for example in the filling apparatus 26 of the tablet press. By means of another mass sensor, arranged for example at the outlet of the tablet press, that counts the ejected tablets and if applicable also measures their weight, the ejected tablets 48 can be assigned to certain mass units 64, 66 previously introduced into the installation via the product inlets 52, 54, and therefore to the corresponding product batch of these mass units 64, 66. if for example one or more mass units are recognized as being faulty by sensors of the installation during their progress through the installation, it is thereby possible to reliably identify the tablets produced from these mass units so that they can be removed from the produced tablets.

While tracking the progress of the mass units in the installation, a specific backmixing of product between different mass units can also be taken into account that is generally specific to the installation. The same holds true with regard to the dead spaces for product that are generally specific to the installation, or a product loss in the installation that is also generally specific to the installation.

Of course the above-explained division of the product into the mass units and the corresponding tracking of the mass units in the installation, as well as the assignment of the produced tablets to certain mass units by the evaluation and control apparatus 60 is performed based on corresponding models saved in the form of algorithms.

The mass units 64, 66, 68, 70 can all have the same mass. The mass of the mass units can preferably be less than 20 g, more preferably less than 10 g, for example about 1 g. The installation is in particular an installation for continuous tablet production. It can also be a containment installation.

Figure 3:
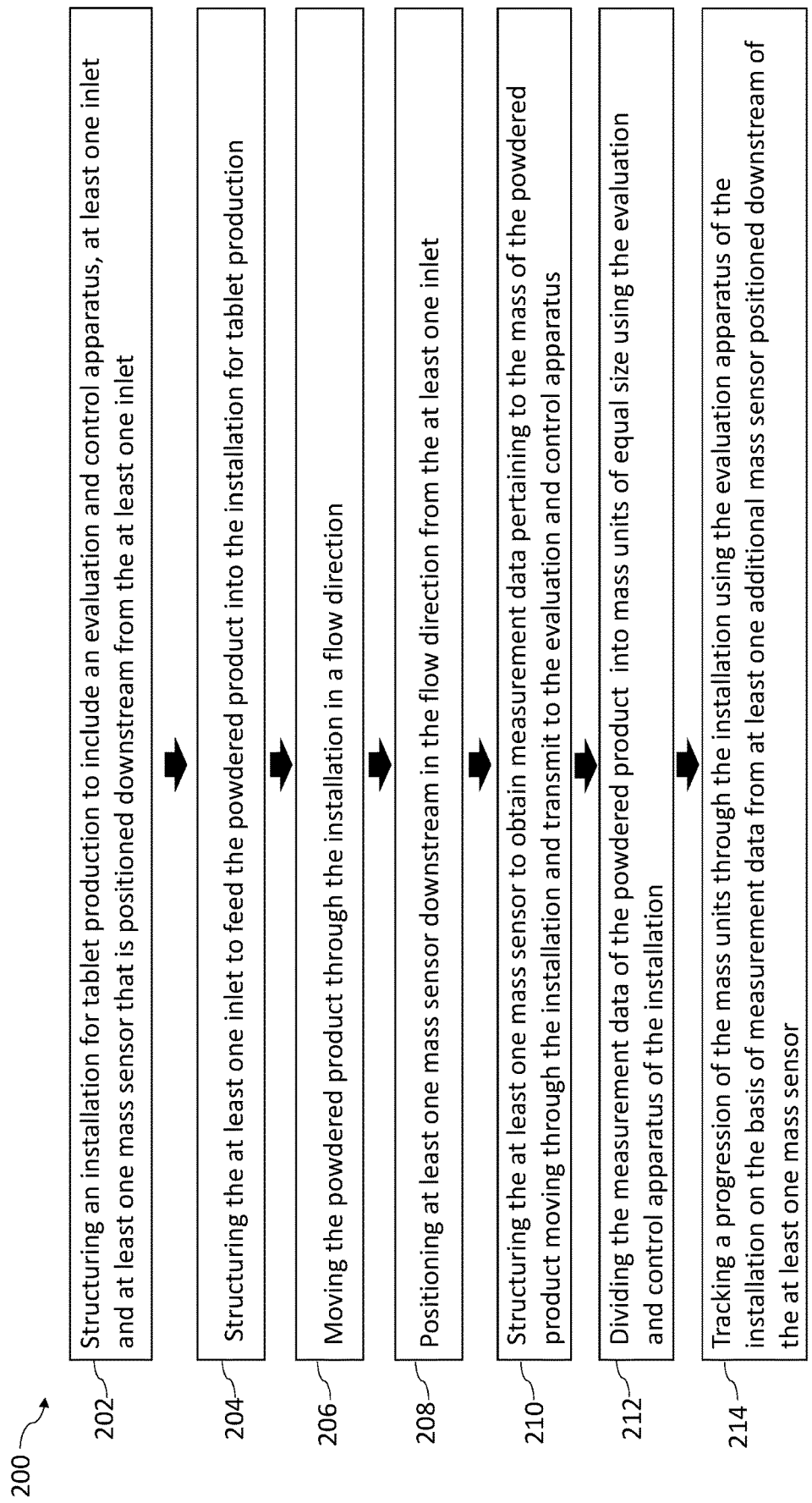
FIG. 3 illustrates a flow chart of an embodiment of the method for product tracking in an installation for tablet production.

With reference to FIG. 3, a method 200 of tracking powdered product in an installation for tablet production 62 is illustrated. At 202, the installation is structured to include an evaluation and control apparatus 60, at least one inlet 52, 54, and at least one mass sensor 100 positioned downstream of the at least one inlet. At 204, the at least one inlet is structured to feed the powdered product into the installation for tablet production. At 206, the powdered product is moved through the installation in a flow direction. The at least one mass sensor 100 is positioned downstream in the flow direction from the at least one inlet 52, 54 at 208. At 210, the at least one mass sensor 100 is structured to obtain measurement data pertaining to the mass of the powdered product moving through the installation. The measurement data of the powdered product is divided at 212 into mass units of equal size 64, 66 using the evaluation and control apparatus 60. At step 214, additional measurement data for the powdered product is obtained by the at least one additional mass sensor and transmitted to the evaluation and control apparatus 60. The at least one additional mass sensor is positioned downstream from the at least one mass sensor. The progression of the mass units is tracked through the installation using the evaluation and control apparatus 60 of the installation on the basis of the additional measurement data from the at least one other mass sensor within the installation.

LIST OF REFERENCE SIGNS

10 Die plate
11 Housing
12 Receiving means
14 Upper punches
16 Lower punches
18 Upper punch guide
20 Lower punch guide
22 Upper control cam elements
24 Lower control cam elements
26 Filling apparatus
28 Filling reservoir
30 Filling chamber
32 Filling pipe
34 Pressing apparatus
36 Upper pre-pressing roller
38 Lower pre-pressing roller
40 Upper main pressing roller
42 Lower main pressing roller
44 Ejection apparatus
46 Scraping apparatus
48 Tablets
50 Discharge apparatus
52 Product inlet
54 Product inlet
56 Mixing apparatus
58 Feed line
60 Evaluation and control apparatus
62 Tablet press
64 Mass units
66 Mass units
68 Mass units
70 Mass units

The invention claimed is:

1. A method for tracking a powdered product in an installation in which the powdered product is processed into manufactured items, the method comprising:
    introducing the powdered product into the installation through at least one inlet;
    moving the powdered product through the installation in a flow direction;
    positioning at least one mass sensor downstream in the flow direction from the at least one inlet;
    obtaining measurement data for the powdered product by at least one mass sensor positioned in the at least one inlet and transmitting the measurement data to an evaluation and control unit;
    dividing the measurement data of the powdered product fed into the installation into mass units of equal size using the evaluation and control apparatus of the installation;
    positioning at least one additional mass sensor downstream in the flow direction from the at least one mass sensor;
    obtaining additional measurement data for the powdered product by the at least one additional mass sensor and transmitting the additional measurement data to the evaluation and control apparatus; and
    tracking a progression of the mass units through the installation using the evaluation and control apparatus of the installation based on the additional measurement data from the at least one additional mass sensor within the installation.

2. The method according to claim 1, wherein the progression of the mass units in the installation is tracked in real time.

3. The method according to claim 1, wherein the installation is configured for tablet production in which the powdered product is pressed into tablets in a tablet press.

4. The method according to claim 3, wherein the progression of the mass units through the installation is tracked using measurement data from another mass sensor arranged at a tablet outlet of the tablet press.

5. The method according to claim 3, wherein the progression of the mass units through the installation is tracked using measurement data from another mass sensor arranged on a filling apparatus of the tablet press.

6. The method according to claim 1, wherein the installation is configured for capsule production in which the powdered product is added to capsules in a capsule filling machine.

7. The method according to claim 1, wherein the installation comprises multiple product inlets for different powdered products and a mixing apparatus for mixing the different powdered products into manufactured items before processing, and wherein the powder product is divided into mass units of equal size using measurement data from several inlet mass sensors arranged at the multiple product inlets.

8. The method according to claim 7, wherein the progression of the mass units through the installation is tracked using measurement data from at least one additional mass sensor arranged on the mixing apparatus.

9. The method according to claim 8, wherein tracking the progression of the mass units through the installation further comprises determining new mass units resulting from mixing of different mass units in the mixing apparatus .

10. The method according to claim 9, wherein tracking the progression of the mass units through the installation further comprises determining a mixing ratio produced by the mixing apparatus.

11. The method according to claim 9, wherein tracking the progression of the mass units through the installation further comprises determining a moving average comprised of sequential mass units.

12. The method according to claim 1, wherein tracking the progression of the mass units through the installation further comprises determining a backmixing of different mass units.

13. The method according to claim 1, wherein tracking the progression of the mass units through the installation further comprises determining dead spaces for product collection.

14. The method according to claim 1, wherein tracking the progression of the mass units through the installation further comprises determining a product loss due to a suction apparatus of the installation.

15. The method according to claim 14, wherein the product loss is determined by comparing a mass flow into the installation for a given product quantity with a number and weight of manufactured items leaving the installation.

16. The method according to claim 15, wherein the mass of the mass units is between 1 g and 20 g.

17. The method according to claim 1, wherein the at least one inlet comprises at least one dosing apparatus.

18. The method according to claim 17, wherein the at least one dosing apparatus is a loss-in-weight feeder.

19. The method according to claim 1, wherein the installation is configured to continuously processes the powdered product into the manufactured items.

20. The method according to claim 19, wherein the installation is configured as a containment installation.

* * * * *